United States Patent [19]

Panzera et al.

[11] Patent Number: 5,176,747
[45] Date of Patent: Jan. 5, 1993

[54] DENTAL PORCELAIN FOR TITANIUM AND TITANIUM ALLOYS

[75] Inventors: Carlino Panzera, Belle Mead, N.J.; Arun Prasad, Cheshire, Conn.

[73] Assignee: American Thermocraft Corporation, Somerset, N.J.

[21] Appl. No.: 738,541

[22] Filed: Jul. 31, 1991

Related U.S. Application Data

[62] Division of Ser. No. 629,617, Dec. 18, 1990.

[51] Int. Cl.⁵ .................. C09K 3/00; C03C 3/076; C03C 3/093
[52] U.S. Cl. .................. 106/35; 501/14; 501/55; 501/67; 501/154; 433/212.1; 433/222.1
[58] Field of Search .................. 501/1, 4, 6, 14, 17, 501/18, 26, 55, 67, 133, 141; 106/35; 433/222.1, 212.1, 228.1, 202.1; 428/433

[56] References Cited

U.S. PATENT DOCUMENTS

| | | | |
|---|---|---|---|
| 4,215,033 | 7/1980 | Bowen | 260/42.15 |
| 4,361,654 | 11/1982 | Ohmura et al. | 501/21 |
| 4,431,451 | 2/1984 | Mabie et al. | 106/35 |
| 4,814,298 | 3/1989 | Nelson et al. | 501/17 |
| 5,009,709 | 4/1991 | Ibsen et al. | 106/35 |

Primary Examiner—Mark L. Bell
Assistant Examiner—Michael A. Marcheschi
Attorney, Agent, or Firm—Watson, Cole, Grindle & Watson

[57] ABSTRACT

Porcelain compositions suitable for use as porcelain layers on metal base dental restorations have fusion temperatures of about 800° C. and lower. The compositions may be employed as coatings on titanium and titanium alloy bases since the compositions have thermal expansion values close to those of titanium and its alloys. A method is also provided for forming dental restorations with relatively inexpensive and biocompatible metal bases and low fusing dental porcelains.

16 Claims, No Drawings

DENTAL PORCELAIN FOR TITANIUM AND TITANIUM ALLOYS

This application is a divisional application of application Ser. No. 629,617, filed Dec. 18, 1990 pending.

This invention relates to dental porcelains having thermal expansion values near that of titanium. More particularly, the present invention relates to dental porcelains which have a low fusion temperature and which fluoresce like natural dentition.

BACKGROUND OF THE INVENTION

Dental crown and bridge restorations are often made with a metal base having a jacket or covering of dental porcelain so that the restoration will closely resemble a natural tooth. Such restorations are well known and have been used for many years.

The general technique for the construction of a porcelain coated dental restoration (i.e. crown or bridge), involves first taking an impression of a denture area that has been prepared to receive the restoration. A die is prepared from the impression, and a metal base ("coping") is cast to fit this die. The metal base has an internal shape to match the prepared denture. A porcelain powder is then mixed with water to form a slurry which is then applied to the metal base by standard procedures. The slurry is shaped in the form of the finished crown or multiple unit bridge. The porcelain is then dried, and fired in a furnace at a desired firing temperature. The crown or bridge may be fired several times before the final form is obtained, and the porcelain may be applied in several layers.

There is a significant temperature change from the firing temperature to room temperature, as a restoration is alternately cooled and fired. Therefore, significant stress can be induced in the restoration if the thermal expansion of the porcelain coating does not closely match that of the metal base.

Metal bases that are most often employed today in such restorations include gold, high and low gold alloys including gold-palladium alloys, silver-palladium alloys, high palladium alloys, nickel-chrome-molybdenum type alloys, gold-silver-palladium alloys and palladium-copper alloys. Gold and its alloys are preferred metals for a metal base due to their biocompatibility with the human body. Gold, however, is a very expensive metal and, like other metals typically used for dental restorations, it requires high fusing temperatures to bond with a jacket or covering of dental porcelain. These metals and alloys exhibit thermal expansion coefficients of about $14 \times 10^{-6}$ in/in/° C. and thus ceramics used in combination therewith have similarly high thermal expansion coefficients.

Current commercially available dental porcelains have fusion temperatures in the range of 1700° F. and up. High fusion temperatures of today's dental porcelains prevent their use with certain metals which readily oxidize at high temperatures.

It is therefore desirable to provide dental restoration which comprises a metal base, or coping, which is biocompatible with the human body and which is not very expensive. It is also desirable to provide a dental porcelain which may be used with an inexpensive, biocompatible metal having a low fusion temperature. The present invention also relates to a dental porcelain which has a low fusing temperature and which bonds securely to a metal base.

SUMMARY OF THE INVENTION

The present invention provides a dental restoration which has a metal base made of titanium or a titanium alloy. The restorations of the present invention also comprise porcelain materials which have thermal expansion coefficients close to that of titanium and fusion temperatures of less than 800° C. The porcelains of the present invention tend to absorb oxygen while fusing which advantageously reduces the amount of titanium oxidation during fusing. The porcelains of the present invention also provide a variable degree of fluorescence so as to closely resemble natural dentition. The present invention also provides a method for preparing dental restorations.

Yet another aspect of the present invention relates to a method of making a dental restoration wherein a titanium or titanium alloy metal base is coated with a dental porcelain and heated to a fusing temperature of less than 800° C.

DETAILED DESCRIPTION OF THE INVENTION

According to an embodiment of the present invention, titanium or a titanium alloy is used as the metal base for a dental restoration. Titanium and most of its alloys are extremely biocompatible, and provide the strength and longevity necessary for dental restorations. Unlike precious metals such as gold, titanium and its alloys are relatively inexpensive. Current, commercially available dental porcelains are not compatible with titanium or its alloys because thermal expansion and fusion temperatures of these porcelains are too high.

The present invention also provides a dental porcelain which has a thermal expansion coefficient close to that of titanium (approximately $9.91 \times 10^{-6}$ in/in/° C. room temperature to 570° C.) and a fusion temperature of less than 850° C., preferably less than 800° C. When heated to more than 800° C., titanium readily oxidizes and also transforms from an alpha crystalline structure to a less-useful beta crystalline structure. Therefore, when using a titanium metal base, it is desired to employ a dental porcelain having a fusion temperature of less than 800° C. (approximately 1470° F.). The present invention also provides a dental porcelain which absorbs oxygen rather than produces oxygen to even further minimize the amount of oxidation of the titanium.

Of the titanium alloys useful in accordance with the present invention titanium 6.4 is a preferred alloy. Titanium 6.4 comprises 6 percent aluminum, 4 percent vanadium and the remainder is titanium. Other titanium alloys may be used provided they have low fusing temperatures and thermal expansion coefficients. Another preferred alloy comprises 5 percent aluminum and 2.5 percent tin.

Preferred dental porcelains according to the present invention preferably comprise oxides of silicon, boron, sodium, potassium, cerium, zinc, titanium, zirconium and tin. Various combinations of these oxides may be employed according to the present invention provided they form porcelains having a thermal expansion coefficient close to that of titanium and a fusion temperature of less than 800° C.

Silicon dioxide is a major component of porcelains according to the present invention. Silicon dioxide has a fusion temperature of approximately 1700° C., much too high to be compatible with titanium independently.

According to the present invention, porcelains comprising greater than about 50 percent silicon dioxide are preferred. Porcelains having silicon dioxide present in an amount of between about 58 and about 65 percent by weight are more preferred, while those having about 61 percent are most preferred.

Aluminum oxide may also be used in porcelains according to the present invention, however, it is not necessary. If used, amounts between about one and about four percent by weight are preferred, about two percent being most preferred.

In order to reduce the fusion temperature of the porcelains of the present invention, boron oxide ($B_2O_3$) and sodium oxide ($Na_2O$) may be added to the porcelain mixtures. Boron oxide is also used to increase the durability of a dental porcelain. Preferably, boron oxide is present in an amount of between about seven and about 13 percent by weight of the porcelain mixture although amounts of up to 30 percent may be used. Most preferably, boron oxide is present in an amount of about nine percent by weight. Sodium oxide is preferably present in an amount of up to about 12 percent by weight, most preferably, about eight percent. If no sodium oxide is used, the weight percent of boron oxide, potassium oxide or both may be increased.

According to the present invention, potassium oxide ($K_2O$) may be used and is preferably present in an amount of up to about eight percent by weight. Preferably, potassium oxide is present in an amount of about six percent by weight. If no potassium oxide is used, the weight percent of boron oxide, sodium oxide, or both may be increased.

To increase the bonding strength of porcelains according to the present invention, cerium oxide and zinc oxide may be added to the porcelain mixtures prior to dissolving. Only a small amount of cerium oxide is necessary to greatly improve bonding strength. Cerium oxide is preferably present in an amount of between about one and about three percent by weight, two percent being more preferred. Zinc oxide is preferably present in greater amounts such as about eight to about eleven percent by weight although amounts of at least eight percent by weight may be used. About nine percent by weight zinc oxide is most preferred.

Titanium oxide is also useful in porcelains according to the present invention Amounts of titanium oxide up to about four percent by weight may be used. The amount of titanium oxide preferred is between about two and about four percent by weight, three percent being most preferred.

Zirconium oxide and a complex of yttrium oxide and cerium oxide are optional ingredients. If used, the zirconium oxide is present in an amount of up to about one percent by weight, preferably about 0.5 percent by weight. Zirconium oxide is primarily used as an opacifier for the porcelain. The yttrium oxide-cerium oxide complex may be used to add fluorescence to the porcelains. If used, amounts of up to only about one percent by weight are necessary to provide dentition having natural-looking fluorescence. About 0.3 percent by weight of the complex is most preferred.

The above mixtures make up body porcelains which may be used in combination with a titanium or titanium alloy base. Preferred body porcelain materials of the present invention have the following compositions:

| COMPONENT | WEIGHT PERCENT BROAD | PREFERRED | MORE PREFERRED |
|---|---|---|---|
| $SiO_2$ | 50-70 | 58-65 | 61 |
| $Al_2O_3$ | 0-4 | 1-4 | 2 |
| $B_2O_3$ | 7-33 | 7-13 | 9 |
| $Na_2O$ | 0-20 | 6-12 | 8 |
| $K_2O$ | 0-20 | 5-8 | 6 |
| $Ce_2O_3$ | 0-3 | 1-3 | 2 |
| ZnO | 8-11 | 8-11 | 9 |
| $TiO_2$ | 2-4 | 2-4 | 3 |
| $ZrO_2$ | 0-1 | 0-1 | .5 |
| $Y_2O_3$—$Ce_2O_3$ | 0-1 | 0-1 | .3 |

The body porcelain may be formed by mixing the various oxides together with the exception of the opacifier and fluorescing agent which are added later. The mixture of various oxides is then heated until all the oxides melt and dissolve. This temperature may exceed 1500° C. for some combinations of the oxides. Once the oxides melt and fuse together, a uniform clear molten mass is produced. The mass is then cooled to form a clear glass which has a randomly oriented atomic structure and little, if any, crystalline arrangement. The glass is then crushed to form a powder having an average particle size of up to about 70 microns. Preferably, the particles have an average size of between about 15 and about 20 microns. The opacifier and fluorescing agents may then be added if desired. The powder may then be wetted and applied in the form of a paste to a metal base or an opaque ceramic and heated to about 800° C. where it fuses to form a dental restoration. Temperatures as low as about 780° C. may be used to fuse the body porcelain. Typically, the body porcelain is applied to a layer of opaque porcelain which has been painted onto a metal base. The body porcelain may be used by itself, however, greater amounts of pigments would need to be added to the body porcelain so as to disguise the metal base.

In order to improve the bonding between the metal and the porcelain, an opaque porcelain is preferably prepared and used to prime the metal base for bonding with the body porcelain. The opaque porcelain comprises approximately 70 to 80 percent by weight body porcelain. Most preferably, the opaque porcelain comprises about 75 percent by weight body porcelain. The remainder of the opaque porcelain comprises at least one member selected from the group consisting of titanium oxide, cerium oxide, stannic oxide and zinc oxide. Most preferably, all 4 oxides are combined to make up the remaining 20 to 30 percent by weight of the opaque porcelain. When all four oxides are used, the titanium oxide is preferably present in an amount of between about four and about six percent by weight, most preferably about five percent by weight. The cerium oxide is preferably present in an amount of between about four and about six percent by weight, most preferably about five percent by weight. The stannic oxide is preferably present in an amount of between about eight and about 12 percent by weight, most preferably, about 10 percent by weight. The zinc oxide is preferably present in an amount of between about four and about six percent by weight, most preferably, about five percent by weight. In a preferred embodiment, the opaque porcelain comprises seventy-five percent by weight body porcelain and twenty-five percent by weight a mixture of titanium oxide, cerium oxide, stannic oxide and zinc oxide. These 4 oxides are pulverized and mixed with powdered body porcelain and then fused to form the opaque porcelain. When the opaque porcelain is fused to the metal base prior to fusing the body porcelain to the metal base, fusing of the body porcelain to the base is greatly improved. After coating the metal with the opaque porcelain, the body porcelain is then coated on the opaque porcelain and the entire structure is heated to near 800° C.

Preferred opaque porcelain materials of the present invention have the following compositions:

| | WEIGHT PERCENT | | |
|---|---|---|---|
| COMPONENT | BROAD | PREFERRED | MORE PREFERRED |
| Body Porcelain | 70–80 | 70–80 | 71 |
| $TiO_2$ | 0–30 | 4–6 | 5 |
| $Ce_2O_3$ | 0–30 | 4–6 | 5 |
| $SnO_2$ | 0–30 | 8–12 | 10 |
| ZnO | 0–30 | 4–6 | 5 |

To form the opaque porcelain, about 70 to 80 percent by weight of the body porcelain in a powdered form is mixed with about 20–30 percent by weight of a mixture of the four oxides mentioned above with respect to the opaque porcelain. This new mixture is then heated to about 1000° C., below the melting point fuses with the oxide particles to form a hard mass which is opaque. The hard mass is then crushed to form opaque porcelain particles of about the same size as desired for the body porcelain or finer. Particle sizes of about 15 to 20 microns ar preferred. The opaque may be applied to a metal base and fused at temperatures as low as about 800° C.

When applying the opaque porcelain to the metal base, the porcelain is typically first mixed with a liquid vehicle so that it may be applied to the base. The liquid vehicle may comprise water, organic solvents, or other liquid carriers which are inert to the reaction between the porcelain and the titanium. One preferred liquid vehicle is Smooth Touch TM (available from Jeneric/Pentron, Wallingford, Conn.) which comprises water with wetting agents. Upon heating to fusion temperatures, the liquid typically evaporates and is preferably completely removed from the system.

When dental restorations according to the present invention are formed in a furnace, it is preferable to provide a vacuum in the furnace so as to minimize the presence of oxygen. If present, oxygen will oxidize the titanium, particularly on exposed surfaces, which may weaken the bond between the titanium and the porcelain. Nitrogen in the air also reacts with titanium to form titanium nitride. Under vacuum conditions, the amount of nitrogen which can react with titanium may also be minimized. The use of a vacuum in a furnace also decreases the amount of bubbles formed in the porcelain. The dental restorations and porcelains of the present invention may be fired in conventional dental furnaces under much lower temperatures then generally needed for current, commercially available porcelains.

Oxidation of the titanium may also be minimized if the titanium metal base is completely covered with the porcelain upon application of the porcelain to the base. This reduces the amount of titanium surface area available on which oxygen can react. Also, porcelains according to the present invention tend to absorb oxygen and/or shield the alloy from nitrogen or oxygen which further decreases the amount of titanium oxidation and nitride formation.

Pigments may be added to either the body porcelain or the opaque porcelain to form naturally looking restorations of various shades. These pigments are commercially available and well known to those of skill in the art.

Although the methods and compositions in accordance with the present invention have been described in connection with preferred embodiments, it will be appreciated by those skilled in the art that additions, modifications, substitutions and deletions not specifically described may be made without departing from the spirit and scope of the invention defined in the appended claims.

We claim:

1. A biocompatible porcelain composition consisting essentially of:

Component (A) 50–70 percent by weight silicon dioxide,

Component (B) 7–33 percent by weight boron oxide,

Component (C) at least 8 percent by weight zinc oxide,

Component (D) up to 4 percent by weight aluminum oxide,

Component (E) up to 4 percent by weight titanium dioxide,

Component (F) up to 12 percent by weight sodium oxide,

Component (G) up to 8 percent by weight potassium oxide,

Component (H) up to 3 percent by weight cerium oxide,

Component (I) up to 1 percent by weight zirconium oxide, and

Component (J) up to 1 percent by weight of a complex of yttrium oxide and cerium oxide, said composition having a thermal expansion coefficient close to that of titanium and a fusion temperature of less than about 800° C.

2. A porcelain composition as defined in claim 1, wherein Component (C) comprises 8–11 percent by weight of said porcelain composition.

3. A porcelain composition as defined in claim 1, wherein component (D) comprises 1–4 percent by weight of said porcelain composition.

4. A porcelain composition as defined in claim 1, wherein Component (E) comprises 2–4 percent by weight of said porcelain composition.

5. A porcelain composition as defined in claim 1, consisting essentially of Components (A), (B), (C), (D) and (E).

6. A porcelain composition as defined in claim 4, consisting essentially of Components (A), (B), (C), and (E).

7. A biocompatible porcelain composition consisting essentially of a mixture of a first component mixture and a second component mixture, said first component mixture comprising 70–80 percent by weight of said porcelain composition and consisting essentially of:

Component (A) 50–70 percent by weight silicon dioxide,

Component (B) 7–33 percent by weight boron oxide,

Component (C) at least 8 percent by weight zinc oxide,

Component (D) up to 4 percent by weight aluminum oxide,

Component (E) up to 4 percent by weight titanium dioxide,

Component (F) up to 12 percent by weight sodium oxide,

Component (G) up to 8 percent by weight potassium oxide,

Component (H) up to 3 percent by weight cerium oxide,

Component (I) up to 1 percent by weight zirconium oxide, and

Component (J) up to 1 percent by weight of a complex of yttrium oxide and cerium oxide, said second component mixture comprising 20-30 percent by weight of said porcelain composition and consisting essentially of:

Component (K) up to 100 percent by weight titanium dioxide,

Component (L) up to 100 percent by weight cerium oxide,

Component (M) up to 100 percent by weight stannous oxide, and

Component (N) up to 100 percent by weight zinc oxide, said porcelain composition having a thermal expansion coefficient close to that of titanium and a fusion temperature of about 800° C. or lower.

8. A porcelain composition as defined in claim 7, wherein Component (C) comprises 8-11 percent by weight of said first component mixture.

9. A porcelain composition as defined in claim 7, wherein Component (D) comprises 1-4 percent by weight of said first component mixture.

10. A porcelain composition as defined in claim 7, wherein Component (E) comprises 2-4 percent by weight of said first component mixture.

11. A porcelain composition as defined in claim 7, wherein said first component mixture consists essentially of Components (A), (B), (C), (D) and (E).

12. A porcelain composition as defined in claim 7, wherein said first component mixture consists essentially of Components (A), (B), (C) and (D).

13. A porcelain composition as defined in claim 18, wherein said first component mixture consists essentially of Components (A), (B), (C), and (E).

14. A porcelain composition as defined in claim 10, wherein Component (K) comprises from 4 to 6 percent of the total weight of said porcelain composition, Component (L) comprises from 4 to 6 percent of the total weight of said porcelain composition, Component (M) comprises from 8 to 12 percent of the total weight of said porcelain composition, and Component (N) comprises from 4 to 6 percent of the total weight of said porcelain composition.

15. A biocompatible porcelain composition consisting essentially of 50-70 weight percent silicon dioxide, 7-33 weight percent boron oxide, at least 8 weight percent zinc oxide and up to 4 weight percent aluminum oxide, said porcelain composition having a thermal expansion coefficient close to that of titanium and a fusion temperature of less than about 800° C.

16. A porcelain composition as defined in claim 15, comprising 8-11 weight percent zinc oxide.

* * * * *